United States Patent [19]

Schneider et al.

[11] Patent Number: 4,666,910
[45] Date of Patent: May 19, 1987

[54] (2-PHENYL-2-(PYRIDYL-OXY, OR -THIO)-ETHYL)-AMINES AND SALTS THEREOF HAVING ANTI-DEPRESSANT PROPERTIES

[75] Inventors: Claus Schneider, Ingelheim am Rhein; Gerhard Walther, Bingen/Rhein; Karl-Heinz Weber, Gau-Algesheim; Wolf D. Bechtel, Appenheim; Karin Böke-Kuhn, Gau-Algesheim, all of Fed. Rep. of Germany

[73] Assignee: Boehringer Ingelheim KG, Ingelheim am Rhein, Fed. Rep. of Germany

[21] Appl. No.: 645,007

[22] Filed: Aug. 28, 1984

Related U.S. Application Data

[63] Continuation-in-part of Ser. No. 417,176, Sep. 13, 1982, abandoned.

[30] Foreign Application Priority Data

Sep. 28, 1981 [DE] Fed. Rep. of Germany ....... 3138550

[51] Int. Cl.$^4$ ................ C07D 413/12; C07D 401/12; A61K 31/535; A61K 31/44
[52] U.S. Cl. .................... 514/228; 514/238; 514/343; 514/351; 546/281; 546/300; 544/126
[58] Field of Search ........... 546/194, 281, 300; 544/126; 514/237, 318, 351, 352, 343, 228, 238

[56] References Cited

U.S. PATENT DOCUMENTS 2,734,845  2/1956  Bauer et al. .......................... 514/352
2,734,846  2/1856  Auhagen et al. .................... 514/352
3,471,501  10/1969 Miyano et al. ....................... 546/194

OTHER PUBLICATIONS

The Merck Index, Ninth Edition, page 1249, Compound, No. 9404, (1976).

Primary Examiner—Alan L. Rotman
Attorney, Agent, or Firm—Hammond & Littell, Weissenberger & Dippert

[57] ABSTRACT

Compounds of the formula

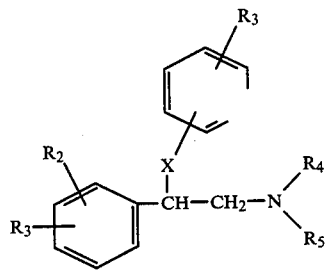

wherein
one of $R_1$ and $R_2$ is hydrogen, halogen, methyl, methoxy, amino or nitro and the other is hydrogen; or $R_1$ and $R_2$ are both halogen;
$R_3$ is hydrogen, halogen or methyl;
$R_4$ and $R_5$ are each independently hydrogen or alkyl or 1 to 2 carbon atoms; or
$R_4$ and $R_5$, together with each other and the nitrogen atom to which they are attached, are pyrrolidino or morpholino; and
X is —O—, —NH—, or —S—;
and non-toxic, pharmacologically acceptable acid addition salts thereof; the compounds as well as their salts are useful anti-depressants.

5 Claims, No Drawings

(2-PHENYL-2-(PYRIDYL-OXY, OR -THIO)-ETHYL)-AMINES AND SALTS THEREOF HAVING ANTI-DEPRESSANT PROPERTIES

This is a continuation-in-part of copending application Ser. No. 417,176 filed Sept. 13, 1982, now abandoned.

This invention relates to novel [2-phenyl-2-(pyridyloxy, -amino or -thio)-ethyl]-amines and acid addition salts thereof, to a method of preparing these compounds, to pharmaceutical compositions containing them as active ingredients, and to a method of using them as antidepressants.

More particularly, the present invention relates to a novel class of compounds represented by the formula

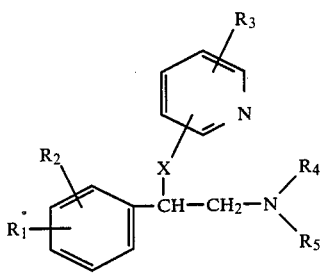

wherein
one of $R_1$ and $R_2$ is hydrogen, halogen, methyl, methoxy, amino or nitro and the other is hydrogen; or $R_1$ and $R_2$ are both halogen;
$R_3$ is hydrogen, halogen or methyl;
$R_4$ and $R_5$ are each independently hydrogen or alkyl of 1 to 2 carbon atoms; or
$R_4$ and $R_5$, together with each other and the nitrogen atom to which they are attached, are pyrrolidino or morpholino; and
X is —O—, —NH—, or —S—;
or a non-toxic, pharmacologically acceptable acid addition salt thereof.

The compounds embraced by formula I may be prepared by reacting a phenylethylamine of the formula

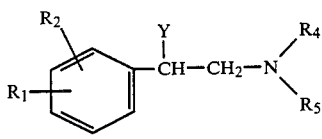

wherein
$R_1$, $R_2$, $R_4$ and $R_5$ have the meanings previousoy defined, and
Y is halogen or hydroxyl,
or an acid addition salt thereof, with a pyridine derivative of the formula

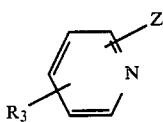

wherein
$R_3$ has the meanings previously defined, and
Z is hydroxyl, amino or mercapto.

In those instances where the starting compound is one of the formula II wherein Y is hydroxyl, the reaction is performed in an acid medium at elevated temperatures. Substances which may be used to provide the acid medium are strong inorganic or organic acids, for instance concentrated mineral acids such as hydrochloric acid, hydrobromic acid, sulfuric acid, or polyphosphoric acid, as well as acetic acid anhydride, phosphorus pentoxide or trifluoroacetic acid.

In those instances where the starting compound is one of the formula II wherein Y is halogen, the reaction is preferably performed in the presence of a basic substance and preferably under phase-transfer conditions, that is, in the presence of one or more long-chain tertiary amines such as a benzyl-tributyl-ammonium halide, a tetrabutyl-ammonium halide or benzyl-triphenyl-phosphonium chloride.

Examples of suitable basic substances are inorganic bases such as alkali metal hydroxides, alkali metal carbonates, alkaline earth metal hydroxides or alkaline earth metal carbonates, and organic bases such as pyridine, piperidine or tertiary amines, or also alkali metal alcoholates.

Compounds of the formula I wherein $R_4$ and/or $R_5$ are hydrogen may be alkylated in the respective positions of the phenyl ring by conventional methods, such as by reaction with a dialkylsulfate or an alkyl halide.

Examples of end products of the formula I which may be obtained by the above-described method are the following:

2-Phenyl-2-[pyridyl-(3)-oxy]-N,N-dimethyl-ethylamine,
2-Phenyl-2-[pyridyl-(2)-oxy]-N,N-dimethyl-ethylamine,
2-(p-Bromophenyl)-2-[pyridyl-(2)-oxy]-N,N-dimethyl-ethylamine,
2-(p-Bromophenyl)-2-[pyridyl-(3)-oxy]-N,N-dimethyl-ethylamine,
2-p-Bromophenyl)-2-[2-chloro-pyridyl-(3)-oxy]-N,N-dimethyl-ethylamine,
2-(p-Bromophenyl)-2-[5-chloro-pyridyl-(2)-oxy]-N,N-dimethyl-ethylamine,
2-(p-Bromophenyl)-2-[6-chloro-pyridyl-(2)-oxy]-N,N-dimethyl-ethylamine,
2-(p-Bromophenyl)-2-[pyridyl-(4)-oxy]-N,N-dimethyl-ethylamine,
2-(p-Chlorophenyl)-2-[pyridyl-(3)-oxy]-N,N-dimethyl-ethylamine,
2-(m,p-Dichlorophenyl)-2-[pyridyl-(3)-oxy]-N,N-dimethyl-ethylamine,
2-Phenyl-2-[pyridyl-(2)-amino]-N,N-dimethyl-ethylamine,
2-Phenyl-2-[pyridyl-(3)-amino]-N,N-dimethyl-ethylamine,
2-(p-Bromophenyl)-2-[pyridyl-(2)amino]-N-methyl-ethylamine,
2-(p-Bromophenyl)-2-[pyridyl-(2)-amino]-N,N-dimethyl-ethylamine,
2-(p-Bromophenyl)-2-[pyridyl-(3)-amino]-N,N-dimethyl-ethylamine,
2-Phenyl-2-[4-methyl-pyridyl-(2)-amino]-N,N-dimethyl-ethylamine,
2-(p-Bromophenyl)-2-[5-methyl-pyridyl-(2)-amino]-N,N-dimethyl-ethylamine,
2-(p-Bromophenyl)-2-[6-methyl-pyridyl-(2)-amino]-N,N-dimethyl-ethylamine,
2-(4-p-Bromophenyl)-2-[5-chloro-pyridyl-(2)-amino]-N,N-dimethyl-ethylamine, 2-(4-p-Bromophenyl)-2-[pyridyl-(2)-thio]-N,N-dimethyl-ethylamine, 2-(p-Bromophenyl)-2-[pyridyl-(3)-oxy]-morpholino-ethylamine, 2-(p-Bromophenyl)-2-[pyridyl-(3)-oxy]pyrrolidino-ethylamine, 2-(p-Bromophenyl)-2-[pyridyl-(2)-amino]-morpholino-ethylamine, 2-(p-Bromophenyl)-2-[pyridyl-(2)-amino]pyrrolidino-ethylamine, 2-(p-Methoxyphenyl)-2-[pyridyl-(3)-oxy[-N,N-dimethyl-ethylamine, 2-(p-Hydroxyphenyl)-2-[pyridyl-(3)-oxy]-N,N-dimethyl-ethylamine, 2-(p-Tolyl)-2-[pyridyl-(3)-oxy]-N,N-diethyl-ethylamine, 2-(p-Nitrophenyl)-2-[pyridyl-(2)-oxy]-N,N-dimethyl-ethylamine, 2-(4-Aminophenyl)-2-[pyridyl-(2)Oxy)-N,N-dimethyl-ethylamine, 2-(m,p-Dichlorophenyl)-2-[pyridyl-(3)-amino]-N,N-dimethyl-ethylamine, and 2-(m,p-Dimethoxyphenyl)-2-[pyridyl-(3)-oxy]-N,N-dimethyl-ethylamine The starting compounds of the formulas II and III are known compounds which are commercially available, or they may be prepared by known methods; see, for example, J. Org. Chem. 1947, (12) 617 ff.

The compounds of the formula I are basic and therefore form addition salts with inorganic or organic acids. Examples of non-toxic, pharmacologically acceptable acid addition salts are those formed with hydrohalic acid, sulfuric acid, phosphoric acid, aminosulfonic acid, formic acid, acetic acid, propionic acid, lactic acid, glycolic acid, gluconic acid, maleic acid, succinic acid, tartaric acid, benzoic acid, salicylic acid, citric acid, ascorbic acid, oxalic acid, p-toluene-sulfonic acid, hydroxyethanesulfonic acid or the like.

The following examples illustrate the present invention and will enable others skilled in the art to understand it more completely. It should be understood, however, that the invention is not limited solely to the particular examples given below.

EXAMPLE 1

2-p-Bromophenyl-2-(3-pyridyloxy)-N,N-dimethyl-ethylamine dihydrochloride

A mixture of 29.9 gm of 2-chloro-2-p-bromophenyl-N,N-dimethyl-ethylamine hydrochloride (0.1 mol), 14.3 gm of 3-hydroxy-pyridine (0.15 mol), 150 ml of an aqueous 25% sodium hydroxide solution, 150 ml of toluene and 0.5 gm of benzyltriphenyl-phosphonium chloride was refluxed for 16 hours. After the solvent had been distilled off from the organic phase, a residue was left behind which was dissolved in ethanol. The dihydrochloride was obtained by adding hydrochloric acid. For purification, the title compound was treated in cyclohexane with activated charcoal and diatomaceous earth. The yield of dihydrochloride was 20 gm (44% of theory). Melting point 128°-129° C. (ethanol).

EXAMPLE 2

2-p-Bromophenyl-2-(2-pyridylamino)-N,N-dimethyl-ethylamine dioxalate

A mixture of 24.5 g of 2-p-bromophenyl-N,N-dimethylethanolamine (0.1 mol) and 11 gm of 2-amino-pyridine (0.11 mol) was heated at 60° C. for 30 minutes in 50 ml of methanesulfonic acid. While still warm, the reaction mixture was poured over ice, made alkaline with ammonia and extracted with ethyl acetate. The product was purified by column chromatography on silica gel/-methylene chloride-ethyl acetate-methanol. The crystalline dioxalate was obtained by the addition of ethanolic oxalic acid.

The yield was 21 gm (42% of theory). Melting point 170°-171° C.

The following table shows additional compounds of the formula I which were prepared from the corresponding starting compounds of the formulas II and III by using procedures analogous to those of Examples 1 and 2.

| Example | $R_1$ | $R_2$ | $R_3$ | $R_4$ | $R_5$ | X | Pyridyl bond | M.p. °C. |
|---|---|---|---|---|---|---|---|---|
| 3 | 4-Br | H | H | H | $CH_3$ | NH | 2 | 181–182 |
| 4 | H | H | H | $CH_3$ | $CH_3$ | O | 2 | 161–162 |
| 5 | H | H | H | $CH_3$ | $CH_3$ | O | 3 | 151–152 |
| 6 | H | H | H | $CH_3$ | $CH_3$ | NH | 2 | 129–130 |
| 7 | H | H | H | $CH_3$ | $CH_3$ | NH | 3 | 123–125 |
| 8 | 4-Br | H | 2-Cl | $CH_3$ | $CH_3$ | O | 3 | 135–136 |
| 9 | 4-Br | H | 5-Cl | $CH_3$ | $CH_3$ | O | 2 | 234–235 |
| 10 | 4-Br | H | 6-Cl | $CH_3$ | $CH_3$ | O | 2 | 193–194 |
| 11 | H | H | 4-$CH_3$ | $CH_3$ | $CH_3$ | NH | 2 | 139–140 |
| 12 | 4-Br | H | 5-Cl | $CH_3$ | $CH_3$ | NH | 2 | 134–136 |
| 13 | 4-Br | H | 5-$CH_3$ | $CH_3$ | $CH_3$ | NH | 2 | 103–104 |
| 14 | 4-Br | H | 6-$CH_3$ | $CH_3$ | $CH_3$ | NH | 2 | 135–136 |
| 15 | 4-Br | H | H | $CH_3$ | $CH_3$ | NH | 3 | 144–145 |
| 16 | 4-Br | H | H | $CH_3$ | $CH_3$ | O | 2 | 162–163 |
| 17 | 4-Br | H | H | $CH_3$ | $CH_3$ | S | 2 | 190–191 |
| 18 | 4-Br | H | H | Morpholino | | O | 3 | 95–97 |
| 19 | 4-Br | H | H | Morpholino | | NH | 2 | 194–195 |
| 20 | 4-Br | H | H | Pyrrolidino | | O | 3 | 152–153 |
| 21 | 4-Br | H | H | Pyrrolidino | | NH | 2 | 117–119 |
| 22 | 4-Br | H | H | $CH_3$ | $CH_3$ | O | 4 | 112 (decomp.) |
| 23 | 4-Cl | H | H | $CH_3$ | $CH_3$ | O | 3 | 126–129 (decomp.) |
| 24 | 3-Cl | 4-Cl | H | $CH_3$ | $CH_3$ | O | 3 | 175–176 |
| 25 | 4-$OCH_3$ | H | H | $CH_3$ | $CH_3$ | O | 3 | 103–105 |
| 26 | 3-Cl | 4-Cl | H | $CH_3$ | $CH_3$ | NH | 3 | 152–153 |
| 27 | 3-$OCH_3$ | H | H | H | H | O | 3 | 222–223 |
| 28 | 4-$CH_3$ | H | H | $CH_3$ | $CH_3$ | O | 3 | 180–181 |

| Example | R₁ | R₂ | R₃ | R₄ | R₅ | X | Pyridyl bond | M.p. °C. |
|---------|------|---|-------|-----|-----|----|------|---------|
| 29 | 4-Br | H | 4-CH$_3$ | CH$_3$ | CH$_3$ | NH | 2 | 219–220 |

The compounds of the present invention, that is, those embraced by formula I above and their non-toxic, pharmacologically acceptable acid addition salts, have useful pharmacodynamic properties. More particularly, they exhibit anti-depressant activity in warm-blooded animals such as mice.

Thus, the compounds of this invention inhibit the ptosis induced in the mouse by tetrabenzaine; the ED$_{50}$ is of the order of 1 mg/kg. This test is used as a standard for antidepressant properties [International Journal of Neuropharmacology 8, 73 (1969)].

The compounds of the instant invention have also shown an exceptionally favorable activity in the test for reserpine antagonism, namely the reversal of the hypothermic effect caused by reserpine by means of a substance with an antidepressant activity. We have also found that they inhibit the re-absorption of serotonin and adrenalin into the neurones.

The new compounds are particularly distinct in that they have a different structure from the antidepressants known up to now; they are equivalent or superior to known commercially available products in their activity, but have a lower toxicity. Particularly effective are those compounds of the formula I wherein R$_1$ is bromine in the p-position, X is oxygen or —NH—, R$_2$ and R$_3$ are hydrogen, and R$_4$ and R$_5$ are methyl, and their non-toxic, pharmacologically acceptable acid addition salts.

Especially effective are the following compounds:
2-(p-bromophenyl)-2-[pyridyl-(3)-oxy]-N,N-dimethyl-ethylamine,
2-(p-bromophenyl)-2-[pyridyl-(2)-amino]-N,N-dimethyl-ethylamine,
2-(p-bromophenyl)-2-[pyridyl-(3)-amino]-N,N-dimethyl-ethylamine,
and their non-toxic, pharmacologically acceptable acid addition salts.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective antidepressant amount of the compounds according to the present invention is from 0,016 to 0,83 mg/kg body weight, preferably 0,083 to 0,5 mg/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 30

Coated Tablets

The tablet core composition is compounded from the following ingredients:

| | |
|---|---|
| 2-(p-Bromo-phenyl)-2-[pyridyl-(3)-oxy]-N,N—dimethyl-ethylamine | 25.0 parts |
| Lactose | 50.0 parts |
| Corn starch | 22.0 parts |
| Gelatin | 2.0 parts |
| Magnesium stearate | 1.0 parts |
| | 100.0 parts |

Preparation

The mixture of active ingredient, lactose and corn starch is granulated with an aqueous 10% gelatin solution through a screen with a 1 mm-mesh, then dried at 40° C. and again passed through a screen. The granulate thus obtained is mixed with magnesium stearate and compressed into 100 mg-tablet cores. The cores thus obtained are coated in the usual way with a thin shell which is applied by using an aqueous suspension of sugar, titanium dioxide, talcum and gum arabic. The finished coated tablets are polished with beeswax. Final weight of coated tablet: 200 mg.

EXAMPLE 31

Tablets

The tablet composition is compounded from the following ingredients:

| | |
|---|---|
| 2-(p-Bromo-phenyl)-2-[pyridyl-(2)-amino]-N,N—dimethyl-ethylamine | 10.0 parts |
| Lactose | 40.0 parts |
| Corn starch | 44.0 parts |
| Soluble starch | 5.0 parts |
| Magnesium stearate | 1.0 parts |
| | 100.0 parts |

Preparation

The mixture of active ingredient and magnesium stearate are granulated with an aqueous solution of the soluble starch, the granulate is dried and intimately mixed with lactose and corn starch. The mixture is then compressed to form tablets weighing 100 mg, each containing 10 mg of active ingredient.

EXAMPLE 32

Suppositories

The suppository composition is compounded from the following ingredients:

| | |
|---|---|
| 2-(p-Bromo-phenyl)-2-[pyridyl-(3)-amino]-N,N—dimethyl-ethylamine | 10.0 parts |
| Suppository base (e.g. cocoa butter) | 1690.0 parts |
| | 1700.0 parts |

Preparation

Using an immersion homogenizer, the finely powdered active ingredient is stirred into the molten suppository base which had been cooled to 40° C. At 35° C.

the composition is poured into slightly pre-cooled suppository molds.

EXAMPLE 33

Injection Solution

The injection solution is compounded from the following ingredients:

| | |
|---|---|
| 2-(p-Bromo-phenyl-2-[pyridyl-(2)-thio]-N,N—dimethyl-ethylamine | 50.0 parts |
| Sodium pyrosulfite | 1.0 parts |
| Disodium salt of ethylenediamine tetraacetic acid | 0.5 parts |
| Sodium chloride | 8.5 parts |
| Double-distilled water   q.s. ad | 1,000.0 parts |

Preparation

The active ingredient and excipients are dissolved in sufficient water, and the solution is adjusted to the desired concentration with the required amount of water. The solution is filtered and filled into 1 cc-ampules under aseptic conditions. Finally, the ampules are sterilized and sealed. Each ampule contains 5.0 mg of active ingredient.

Any one of the other compounds embraced by formula I or a non-toxic, pharmacologically acceptable acid addition salt thereof may be substituted for the particular active ingredient in Examples 30 through 33. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

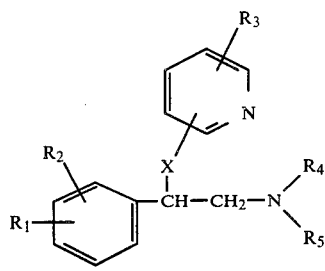

wherein
one of $R_1$ and $R_2$ is hydrogen, halogen, methyl, methoxy, amino or nitro and the other is hydrogen; or $R_1$ and $R_2$ are both halogen;
$R_3$ is hydrogen, halogen or methyl;
$R_4$ and $R_5$ are each independently hydrogen or alkyl of 1 to 2 carbon atoms; or
$R_4$ and $R_5$, together with each other and the nitrogen atom to which they are attached, are pyrrolidino or morpholino; and
X is —O— or —S—;
or a non-toxic, pharmacologically acceptable acid addition salt thereof.

2. A compound of claim 1, where
$R_1$ is p-bromo,
$R_2$ and $R_3$ are hydrogen,
$R_4$ and $R_5$ are methyl, and
X is —O—,
or a non-toxic, pharmacologically acceptable acid addition salt thereof.

3. A compound of claim 1, which is 2-(p-bromophenyl)-2-[pyridyl-(3)-oxy]-N,N-dimethyl-ethylamine or a non-toxic, pharmacologically acceptable acid addition salt thereof.

4. An antidepressant pharmaceutical composition consisting essentially of an inert pharmaceutical carrier in an effective antidepressant amount of a compound of claim 1.

5. The method of preventing or relieving depression in a warm-blooded animal in need thereof, which comprises perorally, parenterally or rectally administering to said animal an effective antidepressant amount of a compound of claim 1.

* * * * *

UNITED STATES PATENT AND TRADEMARK OFFICE
CERTIFICATE OF CORRECTION

PATENT NO. : 4,666,910

DATED : May 19, 1987

INVENTOR(S) : CLAUS SCHNEIDER ET AL.

It is certified that error appears in the above-identified patent and that said Letters Patent is hereby corrected as shown below:

Column 8, line 39: "in an" should read -- in combination with an --.

Signed and Sealed this

Thirty-first Day of May, 1988

Attest:

DONALD J. QUIGG

Attesting Officer

Commissioner of Patents and Trademarks